(12) United States Patent
Garcia-Rodenas (10) Patent No.: US 9,636,367 B2
(45) Date of Patent: *May 2, 2017

(54) COMPOSITION FOR USE IN INCREASING INSULIN SENSITIVITY AND/OR REDUCING INSULIN RESISTANCE

(71) Applicant: NESTEC S.A., Vevey (CH)

(72) Inventor: Clara Garcia-Rodenas, Forel (CH)

(73) Assignee: Nestec S.A., Vevey (CH)

( * ) Notice: Subject to any disclaimer, the term of this patent is extended or adjusted under 35 U.S.C. 154(b) by 283 days.

This patent is subject to a terminal disclaimer.

(21) Appl. No.: 14/352,596

(22) PCT Filed: Oct. 15, 2012

(86) PCT No.: PCT/EP2012/070356
§ 371 (c)(1),
(2) Date: Apr. 17, 2014

(87) PCT Pub. No.: WO2013/057061
PCT Pub. Date: Apr. 25, 2013

(65) Prior Publication Data
US 2014/0286909 A1    Sep. 25, 2014

(30) Foreign Application Priority Data
Oct. 18, 2011  (EP) ................................... 11185603

(51) Int. Cl.
| | | |
|---|---|---|
| *A01N 63/00* | (2006.01) | |
| *A61K 35/745* | (2015.01) | |
| *A61K 31/202* | (2006.01) | |
| *A61K 31/702* | (2006.01) | |
| *A61K 31/7004* | (2006.01) | |
| *A61K 31/7016* | (2006.01) | |
| *A23L 33/00* | (2016.01) | |
| *A23L 33/115* | (2016.01) | |
| *A23L 33/135* | (2016.01) | |
| *A23L 33/21* | (2016.01) | |

(52) U.S. Cl.
CPC .......... *A61K 35/745* (2013.01); *A23L 33/115* (2016.08); *A23L 33/135* (2016.08); *A23L 33/21* (2016.08); *A23L 33/40* (2016.08); *A61K 31/202* (2013.01); *A61K 31/702* (2013.01); *A61K 31/7004* (2013.01); *A61K 31/7016* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | | |
|---|---|---|---|---|
| 5,422,346 A | * | 6/1995 | Mitchell ................ | A23G 3/346 424/464 |
| 6,942,857 B2 | * | 9/2005 | Song .................... | A61K 35/747 424/93.45 |
| 2003/0181401 A1 | * | 9/2003 | Takada .................. | A21D 2/181 514/42 |
| 2007/0254062 A1 | | 11/2007 | Singhal et al. | |
| 2011/0136732 A1 | * | 6/2011 | Boehm .............. | A61K 38/1709 514/4.8 |

FOREIGN PATENT DOCUMENTS

| | | | |
|---|---|---|---|
| EP | 2072052 A1 | * | 12/2007 |
| EP | 2011506 | | 1/2009 |
| EP | 2258216 | | 12/2010 |
| WO | WO 2007/043933 A1 | * | 4/2007 |
| WO | 2007101675 | | 9/2007 |
| WO | WO 2009060073 A1 | * | 5/2009 |
| WO | WO 2010/112429 A1 | * | 10/2010 |

OTHER PUBLICATIONS

Hoffman et al. New England J. Med. (2004) 351: 2179-2186.*
Stutte et al. Eur. J. Pediatrics (2009) 168: 1497-1503.*
Hanefeld Int. J. Clincal Practice (2007) 61: suppl. 153): 20-27.*
International Search Report corresponding to related International Patent Application No. PCT/EP2012/070356 mailed Nov. 27, 2012.
International Written Opinion corresponding to related International Patent Application No. PCT/EP2012/070356 mailed Nov. 27, 2012.

* cited by examiner

*Primary Examiner* — Susan Hanley
(74) *Attorney, Agent, or Firm* — K&L Gates LLP (57) ABSTRACT

The invention discloses a composition comprising at least one long chain polyunsaturated fatty acid, at least one probiotic and a mixture of oligosaccharides, said mixture containing at least one of lacto-N-neotetraose (LNnT) and lacto-N-tetraose (LNT), at least one N-acetylated oligosaccharide different from LNnT and LNT, at least one sialylated oligosaccharide and at least one neutral oligosaccharide, for use in increasing insulin sensitivity and/or reducing insulin resistance. This composition optionally further comprises 2'-fucosyllactose (FL). This composition is particularly adapted for use in infants who were born preterm and/or who experienced IUGR, in pregnant women suffering from gestational diabetes and in children, adolescents, and adults suffering from insulin resistance and/or type II diabetes.

19 Claims, 2 Drawing Sheets

£ different from NS-Cont
different from MS-Cont

COMPOSITION FOR USE IN INCREASING INSULIN SENSITIVITY AND/OR REDUCING INSULIN RESISTANCE

CROSS REFERENCE TO RELATED APPLICATIONS

The present application is a National Stage of International Application No. PCT/EP2012/070356, filed on Oct. 15, 2012, which claims priority to European Patent Application No. 11185603.5, filed Oct. 18, 2011, the entire contents of which are being incorporated herein by reference.

FIELD OF THE INVENTION

This invention relates to a composition for use in increasing insulin sensitivity and/or reducing insulin resistance. This composition is for use in mammals, preferably in humans, more preferably in infants.

BACKGROUND OF THE INVENTION

Eaten carbohydrates from glucidic foods (bread, pasta, potatoes, fruit, sugar . . . ) are transformed into glucose in the intestine during digestion. Glucose passes the intestinal wall and goes into the bloodstream. This provokes glycemia peaks; increases in blood glucose levels which during fasting are approximately 1 g per liter of blood. Insulin is the hormone responsible for lowering blood glucose levels during the course of the metabolic processes following digestion. Increased glycemia during the postprandial period triggers insulin secretion by the pancreas, which induces glucose storage by the body organs, especially liver and muscle. This reverses glycemia to its fasting levels.

In a healthy individual, insulin secretion is proportional to blood glucose levels. The insulin secreted by his pancreas is thus that required to lower glycemia. In some people, insulin response is out of proportion with regards to glycemia.

However, in some individuals, the body tissues do not respond properly to insulin. Insulin receptors in the tissues cease to function adequately and gluco-dependant cells fail to recognize the presence of insulin. As a result, the pancreas needs to secrete more insulin to help glucose enter these cells. The pancreas tries to keep up with this increased demand for insulin by producing more. This phenomenon is called insulin resistance (also known as low insulin sensitivity). Many people with insulin resistance have high levels of both glucose and insulin circulating in their blood at the same time. Eventually, the pancreas fails to keep up with the body's need for insulin, leading to Type II diabetes.

Insulin resistance and Type II diabetes are associated to increased risk of heart attacks, strokes, amputation, diabetic retinopathy, and kidney failure. For extreme cases, circulation of limbs is affected, potentially requiring amputation. Loss of hearing, eyesight, and cognitive ability has also been linked to these conditions According to the World Health Organization, at least 171 million people worldwide suffered from type II diabetes. Its incidence is increasing rapidly, and it is estimated that by 2030, this number will almost double. Insulin resistance is an even more frequent condition, which affected up to 40% adults in the US in 2000. Insulin resistance has been traditionally considered a condition of the middle-old age. However, its prevalence has been dramatically increasing in the pediatric population during the last decades.

A specific case of insulin resistance is the gestational diabetes. Today, 3-10% of pregnancies are affected by abnormal glucose regulation and control.

Infants who were born to mothers with gestational diabetes are at a higher risk than other infants to develop complications. The two main risks these mothers impose on the baby are growth abnormalities and chemical imbalances after birth, which may require admission to a neonatal intensive care unit. Infants who were born to said mothers are at risk of being both large for gestational age (macrosomic) and small for gestational age. Macrosomia in turn increases the risk of instrumental deliveries (e.g. forceps, ventouse and caesarean section) or problems during vaginal delivery (such as shoulder dystocia). Neonates are also at an increased risk of low blood glucose (hypoglycemia), jaundice, high red blood cell mass (polycythemia), low blood calcium (hypocalcemia) and magnesium (hypomagnesemia). Gestational diabetes also interferes with maturation, causing dysmature babies prone to respiratory distress syndrome due to incomplete lung maturation and impaired surfactant synthesis.

Management of insulin resistance in children and adults is essentially based on dietary and lifestyle changes, including healthier dietary habits and increased exercise. These practices can be very efficient in improving insulin sensitivity and in slowing the progression of the disease, but they are difficult to apply and actually not followed by most patients. Type II diabetes can be treated with drugs promoting insulin sensitivity, but their efficacy in reducing the rate of progression of the disease is quite low. Insulin treatment is required during the most advanced phases of the disease.

Some infants, in particular those who were born preterm and/or who experienced intra-uterine growth retardation (IUGR), present a high risk of insulin resistance. Approximately 40% of low-gestation newborns of birthweight less than 1250 g develop hyperglycaemia during the weeks that follow birth. The hyperglycaemia in these newborns is due, in part, to hepatic and peripheral insulin resistance.

Hyperglycaemia in these infants can result in tissular damage. The most common intervention to deal with hyperglycaemia is to decrease the glucose load provided to the infant. This, together with the impaired glucose uptake due to low insulin sensitivity, results in an inadequate energy supply to the infant tissues, which can lead to poor growth and increased risk of complications.

Products containing n-3 polyunsaturated fatty acids, fibers, oligosaccharides and even probiotics have been proposed as nutritional solutions to improve insulin sensitivity and to reduce insulin resistance. However, the efficacy of these nutritional interventions is quite marginal and even controversial, with studies showing no or even deleterious effects.

Thus, there is a need to provide an effective, safe and compliable nutritional solution to improve insulin resistance in infants who were born preterm and/or who experienced IUGR, in pregnant women suffering from gestational diabetes and in children, adolescents, and adults suffering from insulin resistance and/or type II diabetes.

There is also a need for this nutritional intervention in young mammals, in particular infants and children, preferably infants, but also young pets.

SUMMARY OF THE INVENTION

The present inventors have found surprisingly that the administration of a mixture of specific oligosaccharides in combination with at least one long chain polyunsaturated fatty acid (LC-PUFA) and at least one probiotic, is particularly effective in increasing insulin sensitivity and/or reducing insulin resistance.

Accordingly, the present invention provides a composition comprising at least one LC-PUFA, at least one probiotic and a mixture of oligosaccharides, said mixture containing at least one of Galβ1,4GlcNAcβ1,3Galβ1,4Glc (or lacto-N-neotetraose or LNnT), and Galβ1,3GlcNAcβ1,3Galβ1,4Glc (or lacto-N-tetraose or LNT), at least one N-acetylated oligosaccharide different from LNnT and LNT, at least one sialylated oligosaccharide and at least one neutral oligosaccharide, for use in increasing insulin sensitivity and/or reducing insulin resistance.

The composition according to the invention is preferably a nutritional composition.

The LC-PUFA is preferably chosen among arachidonic acid (ARA) and docosahexanoic acid (DHA), more preferably the LC-PUFA is a mixture of ARA and DHA.

The probiotic is preferably chosen among probiotic bacterial strains, more preferably the robiotic is a *lactobacillus* or a *Bifidobacterium* or *Lactobacillus Reuteri*. In a preferred embodiment, the probiotic *Bifidobacterium lactis*.

In one embodiment the oligosaccharide mixture may be derived from animal milk, such as one or more of cow, goat, sheep or buffalo milk. For example, it was obtained by cow's milk fractionation and further enzymatic treatment.

In a second embodiment the oligosaccharide mixture may be prepared using enzymatic, chemo-enzymatic and/or chemical means.

In a third embodiment the oligosaccharide mixture may be prepared using yeast and/or bacterial fermentation technologies. For example, yeast and/or bacterial cells expressing suitable enzymes such as glycosidases and/or glycosyl-transferases upon genetic modification or not might be used to this end.

The composition of the invention is preferably used for infants who were born preterm and/or who experienced IUGR, for pregnant women suffering from gestational diabetes and for children, adolescents, and adults suffering from insulin resistance and/or type II diabetes.

DETAILED DESCRIPTION OF THE INVENTION

As used herein, the following terms have the following meanings. The term "child" means a human between the stages of birth and puberty. An adult is a human older than a child.

The term "infant" means a child under the age of 12 months.

The term "preterm infant" (or "premature infant") means an infant who was born at least than 37 weeks gestational age.

The term "low birth weight infant" means an infant having a liveborn weight less than 2,500 g.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "preterm infant formula" means an infant formula intended for a preterm infant.

The term "human milk fortifier" means a supplement used to increase the calories, protein, minerals and vitamins in breast milk fed to preterm infants or infants with a low birth weight.

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk or the infant formula is partially or totally substituted by other food in the diet of an infant.

The term "increasing insulin sensitivity and/or reducing insulin resistance" means the support for increasing insulin sensitivity and a support for decreasing insulin resistance.

The term "nutritional composition" means a composition which nourishes a subject. This nutritional composition is usually to be taken orally, intragastrically, or intravenously, and it usually includes a lipid or fat source and a protein source.

The term "synthetic mixture" means a mixture obtained by chemical and/or biological means, which can be chemically identical to the mixture naturally occurring in mammalian milks.

The term "hypoallergenic composition" means a composition which is unlikely to cause allergic reactions.

The term "probiotic" means microbial cell preparations or components of microbial cells or microbial cell metabolites with a beneficial effect on the health or well-being of the host. (Salminen S, Ouwehand A. Benno Y. et al. "*Probiotics: how should they be defined*" Trends Food Sci. Technol. 1999:10 107-10).

The term "oligosaccharide" means a carbohydrate having a degree of polymerisation (DP) ranging from 2 to 20 inclusive but not including lactose.

The term "neutral oligosaccharide" means an oligosaccharide having no charge and no N-acetyl residue. It encompasses 2'-fucosyllactose (or FL).

The term "sialylated oligosaccharide" means an oligosaccharide having a sialic acid (such as N-acetylneuraminic acid and/or N-glycolylneuraminic acid) residue.

The term "N-acetylated" oligosaccharide means an oligosaccharide having at least one hexose carrying an N-acetyl residue. It encompasses lacto-N-neotetraose (LNnT) and lacto-N-tetraose (LNT).

All percentages are by weight unless otherwise stated.

In one aspect, the invention provides a composition, comprising:
at least one LC-PUFA,
at least one probiotic, and
a mixture of oligosaccharides, said mixture containing at least one of Galβ1,4GlcNAcβ1,3Galβ1,4Glc (lacto-N-neotetraose or LNnT) and Galβ1,3GlcNAcβ1,3Galβ1,4Glc (lacto-N-tetraose or LNT), at least one N-acetylated oligosaccharide selected from the group comprising GalNAcα1,3Galβ1,4Glc (=3'GalNAc-lac=N-acetyl-galactosaminyl-lactose), Galβ1, 6GalNAcα1,3Galβ1,4Glc (=6'Gal-3GalNAc-lac=galactosyl-N-acetyl-galactosaminyl-lactose), at least one sialylated oligosaccharide selected from the group comprising NeuAcα2,3Galβ1,4Glc (=3'-sialyl-lactose) and NeuAcα2,6Galβ1,4Glc (=6'-sialyllactose), and at least one neutral oligosaccharide selected form the group consisting of Galβ1,6Gal (=β1,6-digalacto-side); Galβ1,6Galβ1,4Glc (=6'Gal-lac); Galβ1,6Galβ1, 6Glc; Galβ1,3Galβ1,3Glc; Galβ1,3Galβ1,4Glc (=3'Gal-lac); Galβ1,6Galβ1,6Galβ1,4Glc (=6',6-diGal-lac); Galβ1,6Galβ1,3Galβ1,4Glc (=6',3-diGal-lac); Galβ1,3Galβ1,6Galβ1,4Glc (=3',6-diGal-lac); Galβ1, 3Galβ1,3Galβ1,4Glc (=3',3-diGal-lac); Galβ1,4Galβ1, 4Glc (=4' Gal-lac) and Galβ1,4Galβ1,4Galβ1,4Glc (=4',4-diGal-lac), for use in increasing insulin sensitivity and/or reducing insulin resistance.

In addition, the composition further comprises Fucα1, 2Galβ1,4Glc (2'-fucosyllactose or FL).

Thus, the oligosaccharide mixture, according to the invention, comprises at least four oligosaccharides, namely at least one of LNnT and LNT, at least one N-acetylated oligosaccharide different from LNnT and LNT, preferably as disclosed above, at least one sialylated oligosaccharide, preferably as disclosed above, and at least one neutral oligosaccharide, preferably as disclosed above.

The oligosaccharide mixture optionally comprises 2'-fucosyllactose, usually in addition to a different neutral oligosaccharide In a second aspect, the invention relates to a composition comprising at least one long chain polyunsaturated fatty acid, at least one probiotic, and an oligosaccharide mixture which comprises:

5-95 wt %, 10-60' wt %, more preferably 20-40 wt %, with respect to the total weight of the oligosaccharide mixture, of one of lacto-N-neotetraose (LNnT) and lacto-N-tetraose (LNT), 0.25-20 wt %, preferably 0.3-10 wt %, more preferably 0.3-5 wt % and even more preferably around 0.5 wt %, with respect to the total weight of the oligosaccharide mixture, of at additional least one N-acetylated oligosaccharide different from LNnT and LNT, 0.5-30 wt %, preferably 0.75-15 wt %, more preferably 0.75-10 wt % and even more preferably around 1 wt %, with respect to the total weight of the oligosaccharide mixture, of at least one sialylated oligosaccharide, and 50-90 wt %, preferably 20-80 wt %, more preferably 10-50 wt % and even more preferably around 50 wt %, with respect to the total weight of the oligosaccharide mixture, of at least one neutral oligosaccharide, for use in increasing insulin sensitivity and/or reducing insulin resistance.

Preferably, the composition further comprises 2'-fucosyllactose (FL), the ratio between (LNnT and/or LNT) and FL being from 0.1:1 to 1.5:1, preferably from 0.2:1 to 1:1.

According to a preferred embodiment, the oligosaccharide mixture is present in an amount of 0.5-70%, more preferably 1-20%, even more preferably 2-5%, with respect to the total weight of the composition.

The oligosaccharide compounds are defined by their structures, where GalNAc is N-acetyl galactosamine, GlcNAc is N-acetyl glucosamine, Gal is galactose, NeuAc is N-acetyl neuraminic acid, Glc is glucose and Fuc is fucose.

The oligosaccharide mixture of the composition according to the invention can be the only source of oligosaccharide in the composition.

The neutral oligosaccharide is preferably chosen among FOS and GOS, preferably GOS such as the ones cited above.

The neutral oligosaccharide of the composition according to the invention may be prepared as a mixture by purchasing and mixing the individual components. For example, synthesised galacto-oligosaccharides such as Galβ1,6Gal, Galβ1,6Galβ1,4Glc, Galβ1,6Galβ1,6Glc, Galβ1,3Galβ1, 3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc and mixtures thereof are commercially available under the trademarks Vivinal® from Friesland Campina, Netherlands, and Elix'or®. Other suppliers of oligosaccharides are Dextra Laboratories, Sigma-Aldrich Chemie GmbH and Kyowa Hakko Kogyo Co., Ltd. Alternatively, specific glycosyltransferases and/or glycosidases, such as galactosyltransferases, and/or fucosyltransferases and/or galactosidases and/or fucosidases may be used to produce galacto-oligosaccharides and/or fucosylated oligosaccharides.

The fucosyllactose is a fucosylated oligosaccharide (that is to say an oligosaccharide having a fucose residue). This fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

According to the invention, the sialylated oligosaccharide can be selected from the group comprising 3'-sialyllactose and 6'-sialyllactose. Preferably, the sialylated oligosaccharide comprises both 3'-sialyllactose and 6'-sialyllactose. In this embodiment, the ratio between 3'-sialyllactose and 6'-sialyllactose lies preferably in the range between 5:1 and 1:2.

The 3'- and 6'-forms of sialyllactose may be obtained by adding to the composition a natural source such as animal milk, or may be isolated by chromatographic or filtration technology from such natural source. Alternatively, they may be produced by biotechnological means using specific sialyltransferases or sialidases, neuraminidases, by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The N-acetylated oligosaccharides of the composition according to the invention may be obtained by adding to the composition a natural source such as animal milk. Alternatively, they may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced through the use of fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP), from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

LNnT and LNT may be synthesised by enzymatic transfer of saccharide units from donor moieties to acceptor moieties using glycosylhydrolases and/or glycosyltransferases as described for example in U.S. Pat. No. 5,288,637 and WO 96/10086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

The composition according to the invention further comprises two oligosaccharides (HMO), selected from the group comprising lacto-N-neotetraose (LNnT), lacto-N-tetraose (LNT), and 2'-fucosyllactose (FL). Preferably said oligosaccharides are LNnT and FL.

Probiotic bacterial strain present in the composition of the invention may be selected from any strain which satisfies the definition of a probiotic and has acceptable shelf-life for the composition in which it will be incorporated. For example, if the composition is incorporated into an infant formulae, said infant formulae is required to remain stable and effective for up to 12 months. The probiotic bacterial strain is preferably a *lactobacillus* or a *bifidobacterium*.

Examples of preferred *Bifidobacterium* species include *Bifidobacterium lactis, Bifidobacterium longum, Bifidobacterium breve* and *Bifidobacterium infantis*, Particularly preferred strains are *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V, the strain of *Bifidobacterium infantis* sold by Procter & Gamble Co. under the trade mark Bifantis and the strain of *Bifidobacterium breve* sold by Institut Rosell (Lallemand) under the trade mark R0070.

Examples of preferred *Lactobacillus* species are *Lactobacillus rhamnosus, Lactobacillus paracasei* and *Lactobacillus reuteri*. Particularly preferred strains are *Lactobacillus rhamnosus* ATCC 53103, *Lactobacillus rhamnosus* CGMCC 1.3724 and *Lactobacillus paracasei* CNCM I-2116.

According to the invention, the probiotic is chosen among probiotic bacterial strains, preferably the probiotic is a *lactobacillus* or a *bifidobacterium* or *Lactobacillus reuteri*, more preferably the probiotic is *Bifidobacterium lactis*.

The probiotic can be present in the composition in a wide range of percentages provided that the probiotic delivers the effect described. However, preferably, the probiotic is present in the composition in an amount equivalent to from 10e2 to 10e12 cfu (=colony forming unit) of probiotic bacterial strain, more preferably between 10e6 and 10e9 cfu, for each gram of the composition. This expression includes the possibilities that the bacteria are alive, inactivated or dead or even present as fragments such as DNA, cell wall materials, intracellular materials or bacteria metabolites. In other words, the quantity of bacteria which the composition contains is expressed in terms of colony forming ability of that quantity of bacteria if all the bacteria were live irrespective of whether they are, in fact, live, inactivated or dead, fragmented or a mixture of any or all of these states.

The composition contains at least one LC-PUFA, which is usually a n-3 or a n6 LC-PUFA. The n-3 LC-PUFA can be a C20 or a C22 n-3 fatty acid. The C20 or C22 n-3 LC-PUFA is preferably present in an amount of at least 0.1 wt % of all fatty acids in the composition. Preferably the n-3 LC-PUFA is docosahexanoic acid (DHA, C22:6, n-3). The n-6 LC-PUFA can be a C20 or a C22 n-6 fatty acid. The C20 or C22 n-6 LC-PUFA is preferably present in an amount of at least 0.1 wt % of all fatty acids in the composition. Preferably the n-6 LC-PUFA is arachidonic acid (ARA, C20:4, n-6). The source of LC-PUFA may be, for example, egg lipids, fungal oil, low EPA fish oil or algal oil. The LC-PUFA of the composition of the invention may be provided in small amounts of oils containing high quantities of preformed arachidonic acid and docosahexanoic acid such as fish oils or microbial oils.

The composition according to the invention is preferably a nutritional composition, more preferably a synthetic nutritional composition. In this case, it can be a preterm infant formula, a human milk fortifier, a starter infant formula, a follow-on formula, a baby food formula, an infant cereal formula, a growing-up milk, a medical food product for clinical nutrition, a yogurt, a soup, a milk-based product, a frozen food, a bar, a breakfast cereal, a canned food, a pet food, or a supplement (including a preterm infant supplement), typically to be used during hospital stay and/or to be used after hospital discharge. A supplement can be for a preterm infant or an infant who has experienced IUGR or a child or a pregnant woman or an adult.

Said composition is preferably a product for preterm feeding such as a preterm infant formula, a human milk fortifier, or a preterm infant supplement. According to an embodiment, the composition is preferably a preterm infant formula, a human milk fortifier, or a supplement. The composition according to the invention can also be products for children or adults such as yogurt or medical food, as well as pets' food.

According to a particularly preferred embodiment, the composition according to the invention is for use in infants who were born preterm and/or who experienced IUGR, in pregnant women suffering from gestational diabetes and in children, adolescents, and adults suffering from insulin resistance and/or type II diabetes.

The composition according to the invention can be for use before and/or during and/or after a weaning period, and/or during childhood, adolescence, pregnancy, and/or adulthood.

The invention includes also the use of a composition according to the invention, as a synthetic nutritional agent, for use in increasing insulin sensitivity and/or reducing insulin resistance.

All the uses stated above are particularly intended for infants who were born preterm and/or who experienced IUGR, pregnant women suffering from gestational diabetes and for children, adolescents, and adults suffering from insulin resistance and/or type II diabetes, in case of humans. But these uses are also intended for pets. The compositions and uses as per the present invention are particularly suited for infants who were born preterm and/or who experienced IUGR, for pregnant women suffering from gestational diabetes and for children, adolescents, and adults suffering from insulin resistance and/or type II diabetes.

Without wishing to be bound by theory, the inventors believe that the efficacy of the combination of oligosaccharide mixture in the composition described above in increasing insulin sensitivity and/or reducing insulin resistance, may be the result of the synergistic combination of immunity modulator effects triggered by the probiotic bacterial strain and the LC-PUFA through their stimulation with the specific oligosaccharide mixture.

The oligosaccharide mixture, the LC-PUFA and the probiotic bacterial strain may be administered in the same composition or may be administered sequentially.

If the preterm and LBW infant group is to be addressed, the composition is preferably a nutritional composition, for example consumed in liquid form. It may be a nutritionally complete formula such as a (preterm) infant formula, a supplement, a human milk fortifier, a follow-on formula or a growing-up milk. Alternatively, for the group of young mammals, the composition may be a pet food.

The composition according to the invention can also contain a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. The proteins can be at last partially hydrolysed in order to enhancement of oral tolerance to allergens, especially food allergens. In that case the composition is a hypoallergenic composition.

The composition according to the present invention can also contain a carbohydrate source in addition to the oligosaccharide mixture. This is particularly preferable in the case where the composition of the invention is an infant formula. In this case, any carbohydrate source conventionally found in infant formulae such as lactose, saccharose, maltodextrin, starch and mixtures thereof may be used although the preferred source of carbohydrates is lactose. In any case, the oligosaccharide mixture is preferably the single source of prebiotic in the composition according to the invention.

The composition according to the present invention can also contain a source of lipids in addition to the LC-PUFA. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added. In the composition, the fat source (including the LC-PUFA such as ARA and/or DHA) preferably has a ratio of n-6 to n-3 fatty acids of about 1:2 to about 10:1, preferably about 3:1 to about 8:1.

The composition of the invention can also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population. If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, gangliosides, polyamines, and the like.

The preparation of the composition according to the invention will now be described by way of example.

The formula may be prepared in any suitable manner. For example, it may be prepared by blending together a protein source, a carbohydrate source (different from the oligosaccharide mixture), and a fat source including the LC-PUFA in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The oligosaccharide mixture will be added at this stage if the final product is to have a liquid form. If the final product is to be a powder, the oligosaccharides may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The oligosaccharide mixture may be added at this stage by dry-mixing along with the probiotic bacterial strain(s), or by blending them in a syrup form of crystals, along with the probiotic bacterial strain(s), and spray-dry (or freeze dry).

If a liquid composition is preferred, the homogenised mixture may be sterilised then aseptically filled into suitable containers or may be first filled into the containers and then retorted.

In another embodiment, the composition of the invention may be a supplement in an amount sufficient to achieve the desired effect in an individual. This form of administration is usually more suited to preterm or LBW or IUGR infants, older children and adults.

The amount of oligosaccharides, LC-PUFA and probiotic bacterial strain to be included in the supplement will be selected according to the manner in which the supplement is to be administered.

The supplement may be in the form of powder, tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The supplement can be added in a product acceptable to the consumer (who is a human or an animal), such as an ingestible carrier or support, respectively. Examples of such carriers or supports are a pharmaceutical or a food or a pet food composition. Non-limiting examples for such compositions are milk, yogurt, curd, cheese, fermented milks, milk based fermented products, fermented cereal based products, milk based powders, human milk, preterm formula, infant formula, oral supplement, and tube feeding.

Further, the supplement may contain an organic or inorganic carrier material suitable for enteral or parenteral administration as well as vitamins, minerals trace elements and other micronutrients in accordance with the recommendations of Government bodies such as the USRDA.

BRIEF DESCRIPTION OF THE DRAWINGS

The advantages, nature, and various additional features of the invention will appear more fully upon consideration of the illustrative experiment now to be described in detail in connection with accompanying drawings. In the drawings:

FIG. 4 uses the results of FIG. 2 and FIG. 3.

EXAMPLE

Experiments were carried out with respect to the effect of the supplementation of a oligosaccharide mixture which is a mixture of cow milk oligosaccharides (CMOS) enriched with galacto-oligosaccharides (demineralized, delactosed whey permeate or DDWP), and 2'-fucosyllactose (FL) and lacto N-neotetraose (LNnT), those two oligosaccharides being added to the mixture DDWP either alone (in two comparative examples) or in combination (according to the invention), LC-PUFA (arachidonic acid ARA- and docosahexaenoic acid -DHA-), and *Bifidobacterium lactis* (BL), on rat pups.

Methodology

EXPERIMENTAL PROTOCOL

The experiments were carried out in agreement with the Swiss Animal Protection Law and were approved by the Office Veterinaire Cantonal (Lausanne, Switzerland, authorization No 2028). Reproductor male and virgin female Long-Evans Hooded rats were purchased from Janvier (France), arriving to the animal care facility two weeks before mating.

Pregnant females received food (Kliba 3437) and water ad libitum, were housed under constant temperature and humidity, and maintained on a 12:12 dark/light cycle. Housing conditions were kept for all the duration of the protocol. At postnatal day (=PND) 2 after birth (B), dams were removed from their maternity cages and the sex of the pups was determined. Standardized litters of 8 male pups were assigned for fostering, after randomizing by body weight. The dams and their pups were assigned to one of two rearing conditions: 1) maternal deprivation groups, exposed to a 180 min period of daily maternal separation on PND2 to PND14 (MS), or 2) unhandled controls (NS).

MS pups were weaned (W) at PND15. They were randomized by weight and nursing dam and distributed into groups of 16 animals which were fed till PND26 with either a control diet (modified AIN 93G, MS-Cont group) or a similar diet adapted to contain LC-PUFA, *Bifidobacterium lactis* CNCM 1-3446 (BL) and oligosaccharides (DDWP, LNnT and/or 2-FL). MS animals (MS-Cont group) were housed in groups of 8 pups up to PND21 to reduce the stress load of the premature weaning and then individually housed until the end of the experiment. Animals from the NS group were weaned onto the control diet (NS-Cont group) at PND21 and individually housed until the end of the experiment.

Animals were sacrificed (554) at PND26 by exhaustive bleeding under isoflurane anesthesia. Blood was sampled at the dorsal aorta in EDTA tubes for further analysis of insulin and glucose levels.

2. Treatment and Diets

The following functional ingredients used for experimental gavage and diet composition comprised DDWP ingredient at 98.8% dry matter, which composition is detailed in Table 1 below.

TABLE 1

Composition of DDWP mixture

| | % of Dry matter |
|---|---|
| Lactose | 33.4 |
| Total oligosaccharides | 25.51 |
| Glucose | 9.06 |
| Galactose | 8.13 |
| Protein | 4.03 |
| Ash | 11.43 |
| Unknown | 8.44 |

The DDWP is typically obtained according to the disclosures of WO2007/101675 or WO 2007/090894 and usually contains a mixture of about 30 wt % of GalNAcα1,3Galβ1,4Glc and Galβ1,6GalNAcα1,3Galβ1,4Glc; 50 wt % of Galβ1,6Galβ1,4Glc and Galβ1,3Galβ1,4Glc; 20 wt % of NeuAcα2,3Galβ1,4Glc and NeuAcα2,6Galβ1,4Glc.

Animals were fed from weaning till the end of the experiment with nutritionally adapted semisynthetic diets (modified AIN 93 G) which composition is shown in Tables 2 and 3

TABLE 2

Diet recipes (per 100 g diet)

| | Control | PUFA-BL-DDWP | PUFA-BL-DDWP-FL | PUFA-BL-DDWP-FL-LNNT |
|---|---|---|---|---|
| K-caseinate (g) | 20.00 | 20.00 | 20.00 | 20.00 |
| Corn starch (g) | 33.95 | 33.95 | 33.95 | 33.95 |
| Maltodextrin (g) | 20.00 | 13.69 | 13.85 | 14.05 |
| Sucrose (g) | 10.00 | 10.00 | 10.00 | 10.00 |
| Lactose (g) | 2.82 | — | 0.28 | 0.56 |
| Glucose (g) | 0.55 | — | 0.06 | 0.11 |
| Galactose (g) | 0.63 | — | 0.06 | 0.12 |
| DDWP (g)[1] | — | 9.94 | 8.95 | 7.95 |
| LNnT (g)[2] | — | — | — | 0.41 |
| FL(g)[3] | — | — | 0.43 | 0.43 |
| Fat mix (g) (see below for composition) | 7.00 | 7.00 | 7.00 | 7.00 |
| Mineral mixture (AIN-93-G) (g) | 3.50 | 3.50 | 3.50 | 3.50 |
| Vitamine mixture (AIN-93-VX) (g) | 1.00 | 1.00 | 1.00 | 1.00 |
| L-Cysteine (g) | 0.30 | 0.30 | 0.30 | 0.30 |
| Cholinhydrogentartrate DAB 10 (g) | 0.25 | 0.25 | 0.25 | 0.25 |
| B. lactis powder (BL) (5.40E+10 cfu/g) (g)[4] | — | 0.37 | 0.37 | 0.37 |
| Total (g) | 100.00 | 100.00 | 100.00 | 100.00 |

[1]DDWP (demineralized, delactosed whey permeate);
[2]LNNT = Lacto-N-neoTetraose;
[3]FL = 2-Fucosyl-Lactose;
[4]B. lactis = BL = B. lactis CNCM I-3446, spray-dried;

TABLE 3

Fat mix (g/100 g fat mix)

| | Control | PUFA-BL-DDWP | PUFA-BL-DDWP-FL | PUFA-BL-DDWP-FL-LNNT |
|---|---|---|---|---|
| Soybean oil | 21.80 | 21.90 | 21.90 | 21.90 |
| Cocoa butter | 37.34 | 27.41 | 27.41 | 27.41 |
| Corn oil | 40.86 | 40.10 | 40.10 | 40.10 |
| ARASCO (PUFA) | — | 5.15 | 5.15 | 5.15 |
| DHASCO (PUFA) | — | 5.44 | 5.44 | 5.44 |

The fatty acid profile of the four diets was balanced to provide similar ratio of n-6/n-3 and similar proportion of saturated, monounsaturated and polyunsaturated fatty acids. Thus, the fatty acid composition of the four diets was nearly the same in terms of fatty acid profile.

The animals were sacrificed on post natal day PND26.

Figure 1:
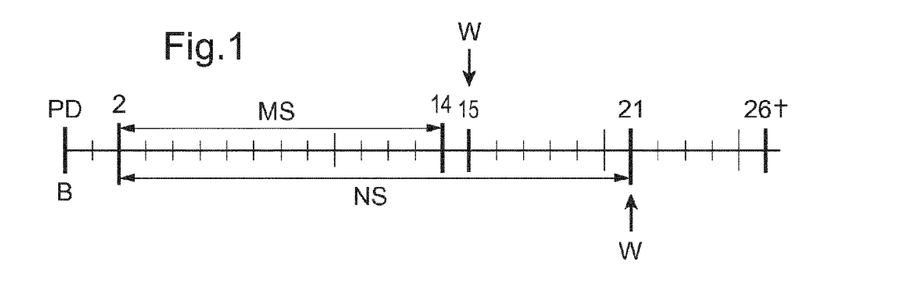
FIG. 1 is a diagram to illustrate the protocol of the experiments.
Figure 2:
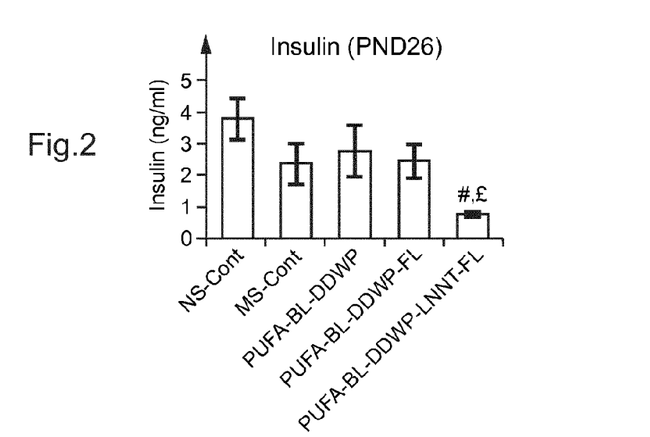
FIG. 2 is a bar graph plotting the results of the experiments, in terms of insulin (ng/ml) in the blood at postnatal day (=PND) 26.
Figure 3:
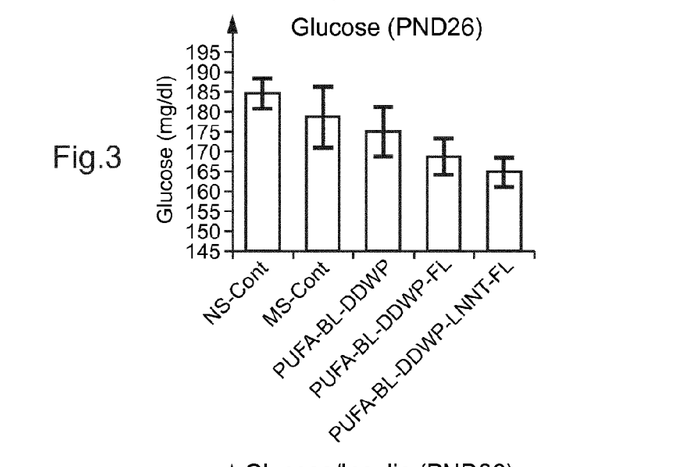
FIG. 3 is a bar graph plotting the results of the experiments, in terms of glucose (ng/ml) in the blood at postnatal day 26.
Figure 4:
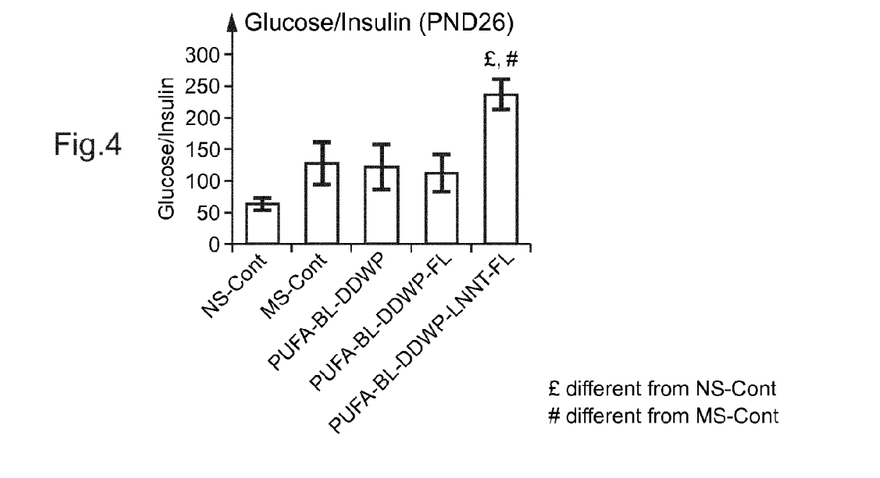
FIG. 4 is a bar graph sharing the ratio glucose/insulin in the blood at postnatal day 26.

From the results on FIGS. 2, 3 and 4, it appears that only the composition PUFA-BL-DDWP-LNnT-FL, according to the invention, show significantly lower insulin and lower glucose content in the blood, as well as the significantly higher glucose/insulin ratio, which indicates increased insulin sensitivity and/or reduced insulin resistance.

The invention claimed is:

1. A method for increasing insulin sensitivity and/or reducing insulin resistance in an individual suffering from insulin resistance, the method comprising administering to the individual a composition comprising at least one long chain polyunsaturated fatty acid (LC-PUFA), at least one probiotic and an oligosaccharide mixture, the mixture containing (i) at least one of Galβ1,4GlcNAcβ1,3Galβ1,4Glc and Galβ1,3GlcNAcβ1,3Galβ1,4Glc (ii) at least one N-acetylated oligosaccharide different from lacto-N-neotetraose (LNnT) and lacto-N-tetraose (LNT), (iii) at least one sialylated oligosaccharide and (iv) at least one neutral oligosaccharide,
    the at least one N-acetylated oligosaccharide different from LNnT and LNT is selected from the group consisting of GalNAcα1,3Galβ1,4Glc, 4Glc and Galβ1,6GalNAcα1,3Galβ1,4Glc, the at least one sialylated oligosaccharide is selected from the group comprising NeuAcα2,3Galβ1,4Glc and NeuAcα2,6Galβ1,4Glc, and the at least one neutral oligosaccharide is selected from the group consisting of Fucα1,2Galβ1,4Glc; Galβ1,6Gal; Galβ1,6Galβ1,4Glc; Galβ1,6Galβ1,6Glc; Galβ1,3 Galβ1,3 Glc; Galβ1,3Galβ1,4Glc; Galβ1,6Galβ1,6Galβ1,4Glc; Galβ1,6Galβ1,3Galβ1,4Glc; Galβ1,3Galβ1,6Galβ1,4Glc; Galβ1,3Galβ1,3Galβ1,4Glc; Galβ1,4Galβ1,4Glc and Galβ1,4Galβ1,4Galβ1,4Glc.

2. The method of claim 1, wherein the at least one neutral oligosaccharide comprises Fucα1,2Galβ1,4Glc.

3. The method of claim 1, wherein the oligosaccharide mixture comprises:
    10-60 wt % with respect to the total weight of the oligosaccharide mixture, of at least one of lacto-N-neotetraose (LNnT) and lacto-N-tetraose (LNT),
    0.25-20 wt % with respect to the total weight of the oligosaccharide mixture, of the at least one N-acetylated oligosaccharide different from LNnT and LNT,
    0.5-30 wt % with respect to the total weight of the oligosaccharide mixture, of the at least one sialylated oligosaccharide, and
    20-80 wt % with respect to the total weight of the oligosaccharide mixture, of the at least one neutral oligosaccharide.

4. The method of claim 3, wherein the at least one neutral oligosaccharide comprises 2'-fucosyllactose (FL), and the ratio between LNnT and/or LNT and the FL is from 0.1:1 to 1.5:1.

5. The method of claim 4, wherein the ratio between the at least one of LNnT and LNT and the FL is from 0.2:1 to 1.0:1.

6. The method of claim 1, wherein the oligosaccharide mixture is 0.5-70% of the total weight of the composition.

7. The method of claim 1, wherein the one LC-PUFA is selected from the group consisting of arachidonic acid (ARA) and docosahexanoic acid (DHA).

8. The method according of claim 1, wherein the at least probiotic is selected from the group consisting of *Bifidobacterium lactis* and *Lactobacillus reuteri*.

9. The method of claim 1, wherein the at least one sialylated oligosaccharide is selected from the group consisting of 3'-sialyllactose and 6'-sialyllactose.

10. The method of claim 1, wherein the at least one neutral oligosaccharide is selected from the group consisting of fructooligosaccharides (FOS) and galactooligosaccharides (GOS).

11. The method of claim 1, wherein the composition is selected from the group consisting of a preterm infant formula, a human milk fortifier, a starter infant formula, a follow-on formula, a baby food formula, an infant cereal formula, a growing-up milk, a medical food product for clinical nutrition, a yogurt, a soup, a milk-based product, a frozen food, a bar, a breakfast cereal, a canned food, a pet food and a supplement.

12. The method of claim 1, wherein the composition is selected from the group consisting of a preterm infant formula, a human milk fortifier, and a supplement.

13. The method of claim 1, wherein the individual is selected from the group consisting of (i) an infant who was born preterm and/or who experienced intra-uterine growth restriction (IUGR, (ii) pregnant women suffering from gestational diabetes, and (iii) children, adolescents, and adults suffering from insulin resistance and/or type II diabetes.

14. The method of claim 1, wherein the individual is selected from the group consisting of (i) pregnant women suffering from gestational diabetes and (ii) children, adolescents, and adults suffering from insulin resistance and/or type II diabetes.

15. The method of claim 1, wherein the oligosaccharide mixture is 1-20% of the total weight of the composition.

16. The method of claim 1, wherein the oligosaccharide mixture comprises:
   20-40 wt. % with respect to the total weight of the oligosaccharide mixture, of at least one of lacto-N-neotetraose (LNnT) and lacto-N-tetraose (LNT),
   0.3-5 wt. % with respect to the total weight of the oligosaccharide mixture, of the at least one N-acetylated oligosaccharide different from LNnT and LNT,
   0.75-10 wt. % with respect to the total weight of the oligosaccharide mixture, of the at least one sialylated oligosaccharide, and
   50-90 wt. % with respect to the total weight of the oligosaccharide mixture, of the at least one neutral oligosaccharide.

17. The method of claim 1, wherein the at least one sialylated oligosaccharide comprises 3'-sialyllactose and 6'-sialyllactose in a ratio between 5:1 and 1:2.

18. The method of claim 1, wherein the individual is an infant or young child.

19. A method for increasing insulin sensitivity and/or reducing insulin resistance in an infant or young child who is predisposed for developing insulin resistance, the method comprising administering to the infant or young child a composition comprising at least one long chain polyunsaturated fatty acid (LC-PUFA), at least one probiotic and an oligosaccharide mixture, the mixture containing (i) at least one of Galβ1,4GlcNAcβ1,3Galβ1,4Glc and Galβ1,3GlcNAcβ1,3Galβ1,4Glc, (ii) at least one N-acetylated oligosaccharide different from lacto-N-neotetraose (LNnT) and lacto-N-tetraose (LNT), (iii) at least one sialylated oligosaccharide and (iv) at least one neutral oligosaccharide wherein,
   the at least one N-acetylated oligosaccharide different from LNnT and LNT is selected from the group consisting of GalNAcα1,3Galβ1,4Glc and Galβ1,6GalNAcα1,3Galβ1,4Glc, the at least one sialylated oligosaccharide is selected from the group comprising NeuAcα2,3Galβ1,4Glc and NeuAcα2,6Galβ1,4Glc, and the at least one neutral oligosaccharide is selected from the group consisting of Fucα1,2Galβ1,4Glc; Galβ1,6Gal; Galβ1,6Galβ1,4Glc; Galβ1,6Galβ1,6Glc; Galβ1,3Galβ1,3Glc; Galβ1,3Galβ1,4Glc; Galβ1,6Galβ1,6Galβ1,4Glc; Galβ1,6Galβ1,3Galβ1,4Glc; Galβ1,3Galβ1,6Galβ1,4Glc; Galβ1,3Galβ1,3Galβ1,4Glc; Galβ1,4Galβ1,4Glc and Galβ1,4Galβ1,4Galβ1,4Glc.

* * * * *